United States Patent [19]

Dowrick

[11] 4,073,920
[45] Feb. 14, 1978

[54] VETERINARY COMPOSITION FOR THE TREATMENT OF MAMMARY DISORDER IN ANIMALS

[75] Inventor: John Sidney Dowrick, Littlehampton, Great Britain

[73] Assignee: Beecham Group Limited, Great Britain

[21] Appl. No.: 712,890

[22] Filed: Aug. 9, 1976

[30] Foreign Application Priority Data

Aug. 14, 1975 United Kingdom ............... 33847/75

[51] Int. Cl.² ...................... A61K 31/43; A61K 47/00
[52] U.S. Cl. .................................... 424/271; 424/365
[58] Field of Search ............................... 424/271, 365

[56] References Cited

U.S. PATENT DOCUMENTS

| | | | |
|---|---|---|---|
| 3,658,555 | 4/1972 | Menz et al. | 424/365 |
| 3,826,845 | 7/1974 | Suyama et al. | 424/365 |
| 3,912,806 | 10/1975 | Dowrick | 424/16 |

FOREIGN PATENT DOCUMENTS 1,110,875  4/1968  United Kingdom.

*Primary Examiner*—Sam Rosen
*Attorney, Agent, or Firm*—Jacobs & Jacobs

[57] ABSTRACT

A veterinary composition for intramammary administration to animals comprising a suspension of a semi-synthetic penicillin in an oily vehicle, the said oily vehicle comprising tri-glycerides, or propylene glycol diesters, of fatty acids containing 8–10 carbon atoms, has a short milk out time, good stability and shelf-life.

20 Claims, No Drawings

VETERINARY COMPOSITION FOR THE TREATMENT OF MAMMARY DISORDER IN ANIMALS

This invention relates to veterinary compositions containing semi-synthetic penicillin suspensions for use in the treatment of mammary disorders in animals, especially bovine mastitis.

Mammary disorders in animals are conventionally treated by the intramammary administration of suspensions or solutions of an antibacterial agent in a suitable vehicle. It has been found that often such antibacterial agents (such as penicillins) are unstable in aqueous vehicles and thus it is necessary to formulate them for intramammary administration in an oily vehicle to produce a product that has an acceptable shelf-life. The oily vehicles used are usually paraffin oils or vegetable oils such as arachis (peanut) oil.

When such products are used during lactation it is important that the antibacterial agent is eliminated as quickly as possible after the treatment has been effected. In this way a minimum of milk is wasted before the level of antibacterial agent in the milk has been reduced to a level acceptable to the health organisations for human consumption.

We have now discovered that semi-synthetic penicillins suspended in a particular class of oily vehicles on intramammary administration to animals give effective treatment of mammary disorders coupled both with a fast milk out rate and also good stability and shelf-life.

Accordingly the present invention provides a veterinary composition for intramammary administration to animals comprising a suspension of a semi-synthetic penicillin in an oily vehicle, the said oily vehicle comprising tri-glycerides, or propylene glycol di-esters, of fatty acids containing 8–10 carbon atoms.

It will be realised by the skilled man that a semi-synthetic penicillin is a penicillin that is normally prepared by the chemical acylation of 6-aminopenicillanic acid, or by an equivalent chemical process. When used herein semi-synthetic penicillin includes a pharmaceutically acceptable salt or ester thereof. Penicillins such as penicillin G and penicillin V which are normally prepared by fermentation are not of course regarded as semi-synthetic penicillins.

The oily vehicle for the semi-synthetic penicillin may comprise a mixture of both tri-glycerides and propylene glycol di-esters of $C_{8-10}$ fatty acids. However, it is normally the case that the oily vehicle will comprise either tri-glycerides of the $C_{8-10}$ fatty acids, or propylene glycol di-esters of the $C_{8-10}$ fatty acids but not both. Preferably these $C_{8-10}$ fatty acids are fully saturated, such as n-caprylic and n-capric acids. Tri-glyceride esters are in general to be preferred to propylene glycol di-esters.

The oily vehicle is conveniently prepared by the commercial fractionating of naturally occuring coconut oil to give mainly $C_{8-10}$ fatty acids followed by esterification of these acids with the chosen alcohol. It will be realised that an oil prepared in this way will contain impurities - oils that do not fall within the class defined above for example - which have not been removed by the fractionating process. We have found that such impurities may be tolerated up to a level of 20% by weight of the total oily vehicle. Thus the oily vehicle will often comprise 80 – 100% of tri-glycerides, or propylene glycol di-esters of $C_{8-10}$ fatty acids and 0 – 20% of such esters of other fatty acids.

Additives may also be present in the oily vehicle in minor proportions. Examples of such additives include conventional thickening agents such as 12-hydroxy stearin, aluminum stearate and colloidal silica, and conventional surfactants such as those sold under the Trade Marks "SPAN" and "TWEEN". "SPANS" are sorbitan fatty acid esters, such as the oleate esters; "TWEENS" are polyoxyalkylene sorbitan fatty acid esters, such as the oleate esters. When the compositions contain additives then they are normally present as up to 10% by weight of the composition. It has been found that the compositions suitably contain 0.1 to 8% by weight, for example 1 to 5% by weight, surfactants. In particular a surfactant mixture of a TWEEN and a SPAN has been found particularly advantageous, with a TWEEN:SPAN ration range of 80:20 to 40:60, preferably 70:30 to 50:50.

Fractionated coconut oil having the desired composition is commercially available. Examples of such oils are the following:

Miglyols, such as Miglyol 812 and Miglyol 810, sold by Dynamit-Nobel;

Neobees, such as Neobee M5 and Neobee 0, sold by PVO International Inc.;

Syndermin/Myritol, such as Syndermin GTC and Myritol 318, sold by Henkel;

Alembicols, such as Alembicol D, sold by Lovelock; and

MCT Oil, sold by Cow and Gate.

All these oils consist essentially of varying proportions of tri-glycerides of n-caprylic and n-capric acids. Miglyol 840 and Neobee M20 are examples of such oils which consist essentially of varying proportions of propylene glycol di-esters of n-caprylic and n-capric acids.

These commercially available oils are very suitable oily vehicles for use in the composition according to the invention. We have found the following to be especially suitable:

Miglyol 812, Syndermin GTC and Neobee M20.

The penicillin used in the composition will be any semi-synthetic penicillin that is known to be effective in the treatment of mammary disorders and that it is compatible with and insoluble in the oily vehicle so that the necessary suspension may be prepared. The composition is particularly useful for the treatment of bovine mastitis and so a penicillin active against this infection will often be used.

Suitable penicillins include the following:

Ampicillin
Amoxycillin
Carbenicillin
Cloxacillin
Flucloxacillin
Ticarcillin
Talampicillin
Nafcillin
Dicloxacillin
Oxacillin
Methicillin
Carfecillin
and mixtures of two penicillins such as:

Ampicillin/Cloxacillin
Amoxycillin/Cloxacillin
Ampicillin/Flucloxacillin
Amoxycillin/Flucloxacillin Ticarcillin/Flucloxacillin The term "semi-synthetic penicillin" when used herein includes pharmaceutically acceptable salts and esters thereof, and thus for example the sodium or potassium salt of a penicillin may often be used in the place of the free penicillin itself.

The most useful penicillins are normally ampicillin, cloxacillin, and penicillin mixtures such as ampicillin/cloxacillin, amoxycillin/cloxacillin; and sodium and potassium salts thereof.

The present invention also provides a process for the preparation of the said veterinary composition, which process comprising suspending a penicillin in an oily vehicle, the said oily vehicle comprising tri-glycerides, or propylene glycol di-esters, of fatty acids containing 8-10 carbon atoms.

This process will be carried out in the usual manner for suspending penicillins in oily vehicles. For example, in a preferred process, the oily vehicle is first sterilised and then a thickening agent added to it with appropriate heating and mixing. Then the chosen semi-synthetic penicillin in sterile form is added to the oily vehicle with appropriate mixing and milling operations, to give the desired suspension.

Lastly, the invention provides a method of treatment of mammary disorders in animals, which method comprises the intramammary administration of an effective amount of a penicillin suspended in an oily vehicle as hereinbefore defined.

For such administration, the chosen suspension will be filled into the tubes or syringe packs of the conventional type for intramammary administration, i.e. provided with a cannula nozzle for insertion into the teat to allow extrusion directly into the mammary gland via the streak canal.

A single dose of the composition will normally contain 1 to 10 gm., preferably 3 to 8 gm., of the suspension. The weight of penicillin in such a unit dose will of course depend on the nature of the disorder to be treated, its severity and the penicillin that is chosen. However, we have found that effective treatment during lactation can usually be obtained with a weight of penicillin in the range 50 to 500 mg. per unit dose. For example, a dose containing about 75 mg. of ampicillin and about 200 mg. of cloxacillin has been found to be particularly effective in the treatment of bovine mastitis.

Often a single dose of the composition of the invention will provide effective treatment of the mammary disorder. However, it is usual practice to repeat the dose at least once (preferably three doses are given), each dosing taking place after milking.

The following Examples illustrate the invention.

EXAMPLE 1

1 kg. of veterinary composition, A, of the following composition was prepared:

|  | % by wt. |
|---|---|
| Sodium ampicilin | 2.5 |
| Sodium cloxacillin | 6.7 |
| 12-Hydroxystearin | 1.0 |
| Miglyol 812 | to 100 |

[Miglyol 812 has the approximate compositon:
Triglyceride of caproic acid: 3% max.
Triglyceride of caprylic acid: 50-65%
triglyceride of capric acid: 30-45%
Triglyceride of lauric acid: 5% max.]

The Miglyol was sterilised by membrane filtration, and to this sterilised Miglyol was added the 12-hydroxystearin at 50° C with high shear mixing. The resultant mixture was allowed to cool, and the semi-synthetic penicillins, in sterile form and finely milled, incorporated therein with mixing to give a suspension of the penicillins in the Miglyol. The suspension was then passed through a colloid mill to produce a fine, homogeneous dispersion.

Packs of syringes suitable for intramammary adminsitration were filled with 3 gm. per syringe of the dispersion.

EXAMPLE 2

In order to compare the milk out time and stability of composition A prepared in Example 1 with a standard preparation, a composition B was prepared in an identical manner to A, but the Miglyol 812 was replaced by arachis oil.

3 gm. of A were administered to the mammary gland of a cow, and it was found that the time taken for the penicillin level in the milk to drop below 0.01 micrograms per ml. was 84 hours. In contrast, this time was 120 hours using an identical procedure but replacing composition A with composition B.

These results show that a substantial fall in the milk out time can be obtained by replacing a conventional oily vehicle with an oily vehicle according to the invention.

The stability of composition A was then compared with the stability of composition B over a period of 12 months at 37° C. Again, a worthwhile improvement was found with composition A:

|  | % Penicillin Remaining | |
|---|---|---|
|  | Ampicillin | Cloxacillin |
| Composition A | 99 | 98 |
| Composition B | 89 | 94 |

EXAMPLE 3

1 kg. of veterinary composition C, of the following composition, was prepared by the method of Example 1. (The surfactant were mixed into the Miglyol at the same time as the 12-hydroxystearin.

|  |  | % by wt. |
|---|---|---|
| Sodium Cloxacillin |  | 6.7 |
| 12-hydroxystearin |  | 1.0 |
| Tween 80 | 58:42 Tween | |
| Span 80 | to Span ratio | 3.0 |
| Miglyol 812 |  | to 100 |

[Span 80 is sorbitan monooleate Tween 80 is polyoxyethylene (20) sorbitan monooleate]

Packs of syringes suitable for intramammary administration were filled with 3 gm. per syringe of the dispersion.

What we claim is:

1. A veterinary composition for intramammary administration to animals for the treatment of mammary disorders in animals comprising a suspension of an effective amount of a semi-synthetic penicillin in an oily vehicle, which oily vehicle comprises triglycerides, or propylene glycol di-esters, of fatty acids containing 8-10 carbon atoms.

2. A composition according to claim 1, wherein the semi-synthetic penicillin is ampicillin, amoxycillin, carbenicillin, ticarcillin, cloxacillin, flucloxacillin, dicloxacillin, oxacillin, talampicillin, nafcillin, methicillin, or carfecillin.

3. A composition according to claim 1, wherein the semi-synthetic penicillin is a mixture of ampicillin and cloxacillin, amoxycillin and cloxacillin, or ticarcillin and flucloxacillin.

4. A composition according to claim 1, wherein the oily vehicle comprises triglycerides or propylene glycol di-esters of n-caprylic and n-capric acids.

5. A method of treatment of mammary disorders in animals, which method comprises the intramammary administration of an effective amount of a composition according to claim 1.

6. A method of treatment of mammary disorders in animals, which method comprises the intramammary administration of an effective amount of a composition according to claim 2.

7. A method of treatment of mammary disorders in animals, which method comprises the intramammary administration of an effective amount of a composition according to claim 3.

8. A method of treatment of mammary disorders in animals, which method comprises the intramammary administration of an effective amount of a composition according to claim 4.

9. A veterinary composition for intramammary administration to animals for the treatment via the teat canal of mammary disorders in animals comprising a suspension of an effective amount of ampicillin, cloxacillin or a salt thereof in an oily vehicle, which oily vehicle comprises tri-glycerides or propylene glycol di-esters, of fatty acids containing 8 to 10 carbon atoms.

10. A composition according to claim 9, comprising a suspension of cloxacillin or a salt thereof in an oily vehicle, which oily vehicle comprises triglycerides, or propylene glycol di-esters, of n-caprylic and n-capric acids.

11. A composition according to claim 9, containing 0.1 to 8% of a surfactant, which surfactant comprises polyoxyalkylene sorbitan fatty acid esters and sorbitan fatty acid esters in a weight ratio of 80:20 to 40:60.

12. A method of treatment of mammary disorders in animals, which method comprises the intramammary administration of an effective amount of a composition according to claim 9.

13. A method of treatment of mammary disorders in animals, which method comprises the intramammary administration of an effective amount of a composition according to claim 10.

14. A method of treatment of mammary disorders in animals, which method comprises the intramammary administration of an effective amount of a composition according to claim 11.

15. A veterinary composition for intramammary administration by syringe via the teat canal to animals in need thereof comprising a suspension of an effective amount of ampicillin and cloxacillin, or salts thereof, in an oily vehicle, which oily vehicle comprises tri-glycerides, or propylene glycol di-esters, of fatty acids containing 8 to 10 carbon atoms.

16. A composition according to claim 15, wherein the fatty acids are n-caprylic and n-capric acids.

17. A composition according to claim 15, containing 0.1 to 8% of a surfactant, which surfactant comprises polyoxyalkylene sorbitan fatty acid esters and sorbitan fatty acid esters in a weight ratio of 80:20 to 40:60.

18. A method of treatment of mammary disorders in animals, which method comprises the intramammary administration of an effective amount of a composition according to claim 15.

19. A method of treatment of mammary disorders in animals, which method comprises the intramammary administration of an effective amount of a composition according to claim 16.

20. A method of treatment of mammary disorders in animals, which method comprises the intramammary administration of an effective amount of a composition according to claim 17.

* * * * *